(12) United States Patent
Subramaniam et al.

(10) Patent No.: US 8,822,734 B2
(45) Date of Patent: Sep. 2, 2014

(54) SINGLE SOLVENT GAS EXPANDED HYDROFORMYLATION PROCESS

(75) Inventors: Bala Subramaniam, Lawrence, KS (US); Raghunath V. Chaudhari, Lawrence, KS (US); Bibhas Sarkar, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 14/001,892

(22) PCT Filed: Feb. 14, 2012

(86) PCT No.: PCT/US2012/024941
§ 371 (c)(1),
(2), (4) Date: Nov. 25, 2013

(87) PCT Pub. No.: WO2012/121838
PCT Pub. Date: Sep. 13, 2012

(65) Prior Publication Data
US 2014/0081050 A1    Mar. 20, 2014

Related U.S. Application Data

(60) Provisional application No. 61/449,118, filed on Mar. 4, 2011.

(51) Int. Cl.
  *C07C 45/50* (2006.01)
  *B01J 19/24* (2006.01)
  *C07C 47/02* (2006.01)

(52) U.S. Cl.
  CPC .............. *C07C 45/505* (2013.01); *B01J 19/24* (2013.01); *C07C 47/02* (2013.01); *C07C 45/50* (2013.01)
  USPC .......................................... 568/454

(58) Field of Classification Search
  USPC ......................................... 568/454
  See application file for complete search history.

(56) References Cited

U.S. PATENT DOCUMENTS

| 7,271,295 B1 * | 9/2007 | White et al. ............... 568/449 |
| 7,365,234 B2 * | 4/2008 | Subramaniam et al. ...... 568/451 |
| 2009/0183430 A1 * | 7/2009 | Schubert et al. ............ 48/85 |

\* cited by examiner

*Primary Examiner* — Sikarl Witherspoon
(74) *Attorney, Agent, or Firm* — William B. Miller

(57) ABSTRACT

Allyl alcohol, particularly from biobased sources such as glycerol, is hydroformylated to products including 4-hydroxybutyraldehyde and 4-hydroxy-2-methylpropionaldehyde by forming a homogeneous reaction mixture including allyl alcohol, a rhodium-based hydroformylation catalyst and a near critical liquefiable petroleum gas or mixture of such gases, reacting the near critical liquefiable petroleum gas (or gas mixture)-expanded allyl alcohol substrate with carbon monoxide and with hydrogen in the presence of the catalyst, and recovering substantially all of the petroleum gas or gases overhead by reducing the pressure and degassing the product mixture. Dense propane is especially useful as a single inert solvent/diluent, and substantially no other solvent/diluent is needed.

19 Claims, 2 Drawing Sheets

SINGLE SOLVENT GAS EXPANDED HYDROFORMYLATION PROCESS

Hydroformylation, or oxo synthesis, is an important industrial process for the production of aldehydes from olefinic substrates. In one well-known embodiment, allyl alcohol is reacted with a carbon monoxide/hydrogen gas mixture in the presence of a catalyst to provide 4-hydroxybutyraldehyde (HBA) and its branched isomer 3-hydroxy-2-methylpropionaldehyde (HMPA). HBA is an important intermediate for producing 1,4-butanediol (BDO) through the hydrogenation of HBA (and from BDO, gamma butyrolactone and polybutylene terephthalate), and while HMPA can likewise be hydrogenated to a useful and marketable product in 2-methyl-1,3 propanediol (MPD), the latter has a much more limited demand and market value compared to BDO. Consequently, a great deal of research has been conducted in recent years in the area of hydroformylating allyl alcohol to HBA and HMPA in order to produce a high linear (normal) to branched (iso) product mix ratio and lesser yields of products other than HBA, generally. Such other products may include n-propanol and propionaldehyde, for example.

U.S. Pat. No. 7,271,295 to White et al. and U.S. Pat. No. 7,279,606 to White, which are both assigned to one of the world's largest producers of BDO, are exemplary of these efforts, describing processes for hydroformylating allyl alcohol which purportedly produce "unexpectedly high" ratios of the more desirable, linear HBA product to the branched HMPA product. The '295 and '606 patents themselves list a number of references describing alternate methods for reducing the yield loss to non-HBA hydroformylation products from allyl alcohol, see, for example, U.S. Pat. No. 6,127,584; U.S. Pat. No. 6,225,509; U.S. Pat. No. 4,306,087; Japan Kokai Nos. 06-279345 and 06-279344. Certain of these references concern improved linear aldehyde yields obtained through the selection and use of particular catalysts, see, for example, the '295 and '606 patents, while others claim improvements through selecting certain process conditions (U.S. Pat. No. 6,225,509 for example) or steps (U.S. Pat. No. 6,127,584).

Conventionally, the hydroformylation of allyl alcohol as described in these and in other like references is carried out in the liquid phase and with homogeneous catalyst systems, with high pressures of synthesis gas/carbon monoxide and hydrogen of between 10 to 100 atmospheres and at temperatures ranging between 40 and 200 degrees Celsius. A common shortcoming, however, is that an inert organic solvent/diluent is used from which the desired HBA product and catalyst must be recovered and then the solvent/diluent recycled for reuse. The amounts of inert organic solvent/diluent. are substantial and costly to separate out for recycle and reuse.

Recently, an improved hydroformylation process has been described in U.S. Pat. No. 7,365,234 to Subramaniam et al., in which an olefin is reacted with carbon monoxide and hydrogen in the presence of a hydroformylation catalyst in a liquid that has been volumetrically expanded with a compressed gas, such as supercritical or subcritical carbon dioxide. Homogeneous reaction systems are contemplated which advantageously include an added, inert solvent, or which do not include an added, inert solvent and rather use the non-polar, olefin substrate as the liquid phase and as a solvent itself. Non-polar solvents are noted as generally favoring higher linear:branched hydroformylation product ratios, and listed solvents overall include (in addition to the olefin substrates themselves) aromatics such as toluene and xylenes, hydrocarbons and mixtures of hydrocarbons which can also serve for "diluting the above-mentioned aldehydes and the downstream products of the aldehydes", alkyl esters of aliphatic carboxylic acids, ethers such as tert-butyl methyl ether and tetrahydrofuran, non-polar alcohol solvents such as methanol, ethanol, n-propanol, isopropanol, n-butanol and isobutanol, and ketones such as acetone and methyl ethyl ketone. Allyl alcohol is mentioned among the olefin substrates that can be hydroformylated, though the examples supplied were of the hydroformylation of 1-octene. The expanding gas can be carbon dioxide, $N_2O$, xenon and $SF_6$, though for reasons of cost and ease of use, pressurized subcritical or supercritical $CO_2$ was indicated to be usually preferred and all of the examples given employed compressed carbon dioxide in fact.

Beneficial effects attributed to the use of subcritical or supercritical carbon dioxide included increased solubility of the hydrogen and carbon monoxide in the liquid reaction phase, thus enabling milder conditions to be used for carrying out the reaction or enhanced rates of reaction/turnover frequencies; an improved environmental and safety profile by displacing volatile organic solvents (VOCs) that would otherwise be required; using the latent heat capabilities of near-critical $CO_2$ to effectively curtail the temperature rise of a highly exothermic reaction and prevent thermal runaway; and surprisingly, given prior published results with hydroformylation of 1-octene in $CO_2$-expanded acetone, the capacity when an excess of the nonpolar substrate/solvent 1-octene was used to adjust, "tune" or select the linear:branched product ratio by varying the content of the compressed gas in the liquid to be volumetrically expanded thereby.

The present invention in one aspect concerns a fundamentally different process for hydroformylating an olefinic feedstock (or substrate), wherein an inert compressed gas serves as both a volumetric expansion medium in the manner of the above-summarized '234 Subramaniam patent, for causing a volumetric expansion of a liquid including and preferably comprised substantially entirely of the olefinic substrate, as well as a solvent/diluent in the reaction mixture—so that the process may be conducted in the substantial absence of any solvent other than the inert, dense gas.

Consequently, in the particular context of the hydroformylation of olefinic substrates like allyl alcohol that can exhibit a substrate-related inhibition effect and thus require an added diluent of some kind, the added expense associated with adding and then removing a typical organic solvent such as toluene can be avoided, along with the safety and environmental hazards and potential impacts associated therewith.

In a second, related aspect, the inert compressed gas is able to be substantially completely recovered overhead from the process as a vapor that can be recycled for being recompressed and reused as desired, through reducing the pressure and degassing the product mixture, in effect reducing a solvent removal step to a simple degassing step as opposed to requiring distillation, extraction, evaporation or other like energy-intensive, more complex and costly solvent removal and recovery measures.

We have found in this regard that ally) alcohol, such as may be derived in preferred embodiments from biobased sources such as glycerol, can effectively be hydroformylated to products including 4-hydroxybutyraldehyde and 4-hydroxy-2-methylpropionaldehyde by forming a homogeneous reaction mixture including ally) alcohol, a rhodium-based hydroformylation catalyst and a liquefiable petroleum gas or mixture of such gases, then reacting the ally) alcohol with carbon monoxide and with hydrogen in the presence of the catalyst under elevated temperature and pressure conditions sufficient to carry out a hydroformylation of the ally) alcohol, with recovering substantially all of the petroleum gases overhead by reducing the pressure and degassing the product mixture.

More particularly, dense propane has been found to be an especially good expansion medium and solvent/diluent in the hydroformylation of ally) alcohol, in the presence of the rhodium catalysts which have been favored commercially for the hydroformylation of allyl alcohol. We have further found that by causing a volumetric expansion of the liquid reaction mixture and tuning the $H_2/CO$ ratio in the expanded reaction mixture according to the methods described in the '234 Subramaniam patent, using near-critical dense propane, and further by limiting the allyl alcohol content in the reaction mixture (as made possible through the use of the compressed or dense gas diluent), the 4-hydroxybutanal:3-hydroxy-2-methylpropanal, linear to branched aldehyde product ratio, can be adjusted by at least 100 percent and can be 10:1 or more, without necessitating any addition of a further organic solvent that would later have to be separated back out from the hydroformylation product mixture.

In a further refinement, homogeneous hydroformylation catalysts are employed which are solubilized in the liquid reaction mixture but which are effectively retained by a filter, for example a nanofiltration membrane, while the products from the hydroformylation of an olefinic substrate are substantially recovered in the permeate. In combination with the capacity to separate and recover substantially all of the inert compressed gas diluent through degassing and with omitting other added solvents/diluents, by this refinement it will be appreciated that the hydroformylation products can be recovered in a form that is suited for being used as a feed for a hydrogenation process to convert, for example, 4-hydroxybutyraldehyde to 1,4-butanediol and 4-hydroxy-2-methylpropionaldehyde to 2-methyl-1,3 propanediol.

Figure 3:
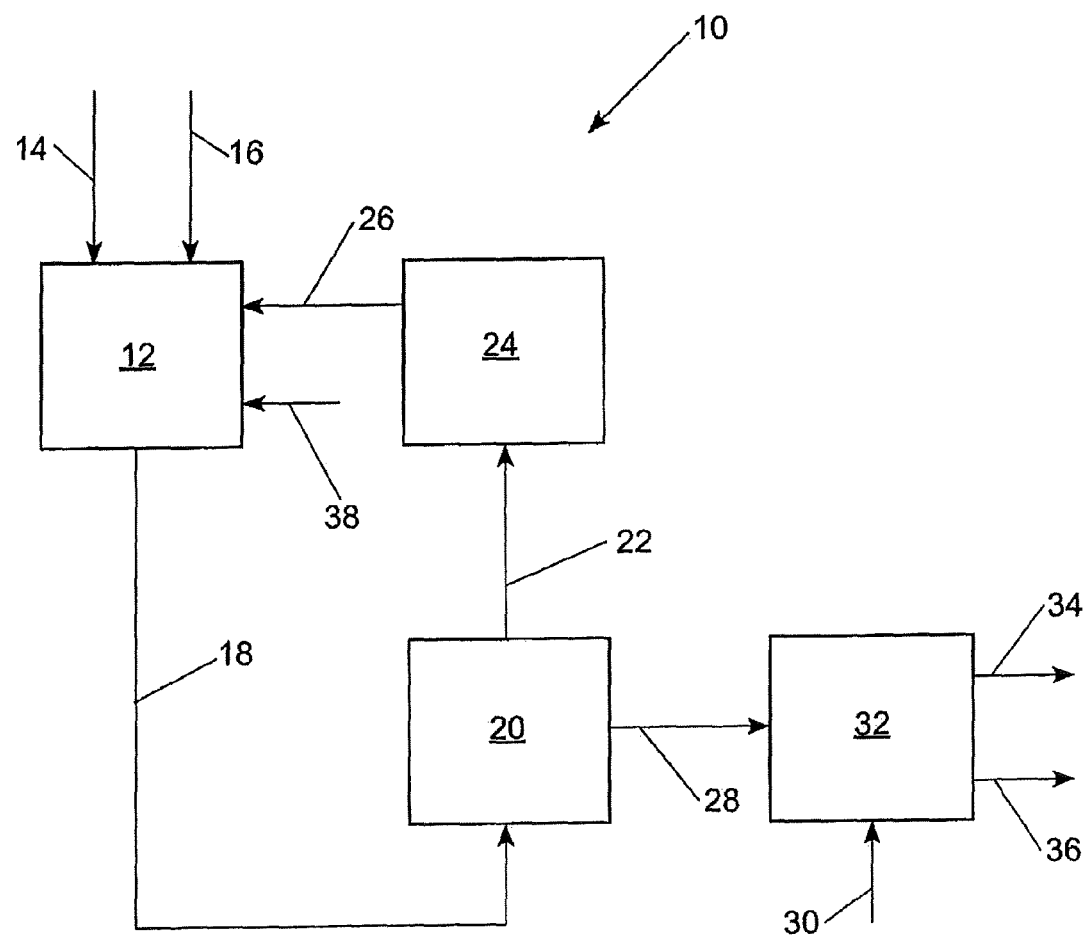

FIG. 3 schematically depicts a preferred embodiment of a continuous hydroformylation process according to the present invention.

Figure 1:
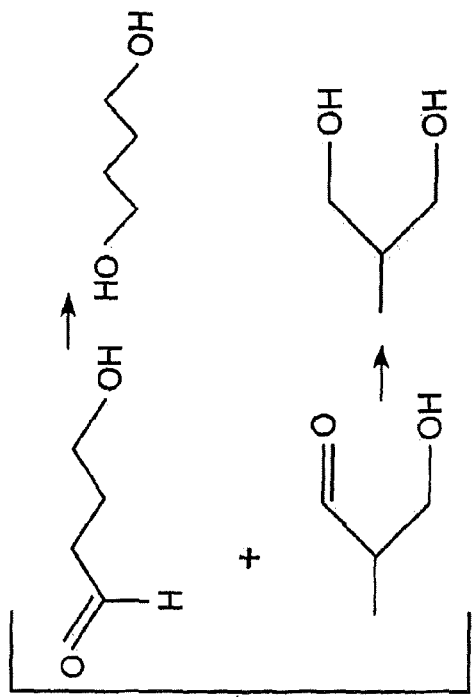
FIG. 1 illustrates the conversions accomplished in preferred process embodiments of the present invention.

In a preferred industrial application of the present invention, as illustrated by the chemical conversions shown in FIG. 1, glycerol such as is produced as a co-product in the production of biodiesel is initially dehydrated to acrolein, and the acrolein in turn hydrogenated to produce allyl alcohol. The allyl alcohol is thereafter hydroformylated according to the present invention, to yield products including the n-aldehyde 4-hydroxybutyraldehyde and the iso-aldehyde 3-hydroxy-2-methylpropionaldehyde. The aldehydes are then preferably hydrogenated to provide 1,4-butanediol and 2-methyl-1,3 propanediol.

With regard to each of these steps, the dehydration of biodiesel-derived glycerol to acrolein has been extensively investigated, and numerous methods are available for accomplishing this initial step. Dubois et al. (on behalf of a commercial producer of acrylic acid, via acrolein derived from propylene) have for example proposed various catalysts and methods for the dehydration of renewable source glycerol to provide acrolein, see, e.g., U.S. Pat. No. 7,396,962 (liquid or gas phase process in the presence of molecular oxygen, using acidic solid catalysts having a Hammett acidity less than +2); WO 2009/127889 (catalyst comprising a salt or salts of heteropolyacid in which protons have been exchanged with one or more of Group 1 to Group 16 cations); WO 2009/044081 (gas phase process with molecular oxygen present, using an iron phosphorus oxide catalyst additionally containing one or more of the alkali metals, the alkaline earth metals, Al, Si, B, Co, Cr, Ni, V, Zr, Sn, Sb, Ag, Cu, Nb, Mo, Y, Mn, Pt, Rh, La, Ce and Sm); WO 2009/044051 (carrying out a reactive vaporization of a solution of glycerol in the presence of an acid catalyst of Hammett acidity less than +2); WO 2008/007002 (using a membrane catalyst for converting glycerol to acrylic acid wherein a first membrane layer includes a catalyst for converting acrolein to acrylic acid, and the second layer formed on the first includes an acid phase with a Hammett acidity of less than +2 for converting glycerol to acrolein); WO 2008/087315 (removal of 40 to 90 percent of water from glycerol dehydration product along with some dehydration byproducts prior to feeding dehydration reaction product to second reactor with catalyst for converting acrolein to acrylic acid); WO 2008/129208 (describing a method for vaporizing an aqueous glycerol solution in a fluidized bed with an inert solid and removing some impurities in the process of vaporizing).

A competing producer of acrylic acid has in like manner proposed other methods and catalysts for the gas phase dehydration of glycerol to acrolein, see, e.g., U.S. Pat. No. 5,387,720 (liquid or gas phase dehydration of 10 to 40 percent glycerol solution in water at up to 340 degrees Celsius over solid acid catalyst having Hammett acidity less than +2), US 2008/0183019 (acidic solid state catalyst with Hammett acidity less than +2 and including tungsten compounds and other promoters); US 2008/0214384 (describing a process for regenerating the same catalyst in an oxidizing or reducing atmosphere). Liquid phase and gas phase dehydration processes have been contemplated, see, e.g., US 2009/0134357 and US 2009/0068440 (describing multistep processes for producing acrolein, acrylic acid and polyacrylates from glycerol), while another major producer of acrylic acid has also been active in developing catalysts and methods for producing acrolein from glycerol, see, e.g., U.S. Pat. No. 7,612,230 (gas phase dehydration of aqueous solution with preferably 10 percent or less of glycerol, catalyzed by a clay compound, a supported phosphoric or sulfuric acid catalyst, an inorganic oxide or inorganic composite oxide or other solid acidic substances such as metal sulfates, carbonates, nitrates and phosphates); US 2009/0118549 (catalyst with one or more metal phosphates from aluminum salts, zirconium salts, manganese salts, certain alkali and alkali earth metal salts) and US 2009/0177015 (crystalline metallosilicate catalysts using one or more of Al, B, Ti, Cr, Fe, Co, Ni, Cu, Zn, Ga, In, P, Sc, V, Ge, As, Y, Zr, Sn, Sb and La, and especially using Al). A process for converting glycerol to acrolein in water and in the presence of an acid catalyst under supercritical conditions has been proposed, see JP 2010-13367A, "Method Production of Acrolein By Using Supercritical Water". Still other methods and catalysts have been investigated by not-for-profit research laboratories as part of an initiative into renewable source based-chemicals production, see, e.g., US 2009/0054538; US 2009/0054694 and Patent Cooperation Treaty Application Serial Number PCT/US10/61373, filed Dec. 20, 2010 for "MULTIHYDRIC COMPOUND DEHYDRATION SYSTEMS, CATALYST COMPOSITIONS, AND METHODS", published as WO 2011/075743 on Jun. 23, 2011 (using a fumed material-supported metal phosphate catalyst comprised of one or more metals from Groups 2-12 and/or Rb, K and Cs, and describing in situ catalyst regeneration methods).

It is considered that any of the above or other known methods for converting renewable source-based glycerol to acrolein may be used as desired, though generally it is expected that those methods producing fewer byproducts and enabling a greater purity allyl alcohol hydroformylation feedstock will be favored, taking into account fouling or deactivating effects that might be associated with a less pure allyl alcohol feedstock on the hydroformylation catalyst.

The next step in the process illustrated in FIG. 1, namely, the hydrogenation of acrolein to allyl alcohol, is also well established, being commercially practiced on an industrial commodity scale from acrolein derived from non-renewable, petroleum-based propylene. U.S. Pat. No. 4,072,727 to Vanderspurt is descriptive of one process for hydrogenating acrolein to allyl alcohol, wherein a supported silver-cadmium-zinc alloy catalyst is employed in a vapor phase process. U.S. Pat. No. 4,731,488 to Shimasaki et al. also describes a vapor phase hydrogen transfer reaction wherein acrolein can be converted to allyl alcohol in the presence of a supported metal oxide catalyst comprised of magnesium, at least one of boron, aluminum, silicon, phosphorus, titanium, vanadium, iron, yttrium, zirconium, niobium, tin, antimony, lead, bismuth, lanthanum and cerium, and optionally an alkali metal or alkaline earth metal other than magnesium. Examples are given wherein acrolein is reacted with isopropanol (as a source of hydrogen) and produces allyl alcohol. Additional methods, including methods carried out in the liquid phase as well as in the vapor phase, are outlined in U.S. Pat. No. 5,892,066 and the references cited therein (including Process Economics Program Report 58, "Glycerine and Intermediates", SRI International (December 1969)). In the '066 patent, particularly, both liquid and vapor phase processes are reported as having been developed; the vapor phase processes use a large excess of hydrogen at 200-300 degrees Celsius and high pressures in the presence of a mixed copper cadmium catalyst, while liquid phase processes use a catalyst containing organic acid salts of copper and cadmium.

The allyl alcohol thus produced is then hydroformylated to products including 4-hydroxybutyraldehyde and 4-hydroxy-2-methylpropionaldehyde as described in greater detail hereafter, by forming a homogeneous reaction mixture including allyl alcohol, a rhodium-based hydroformylation catalyst and a liquefiable petroleum gas or mixture of such gases, then reacting the allyl alcohol with carbon monoxide and with hydrogen in the presence of the catalyst under elevated temperature and pressure conditions sufficient to carry out a hydroformylation of the allyl alcohol. The 4-hydroxybutyraldehyde and 4-hydroxy-2-methylpropionaldehyde are then preferably hydrogenated to provide 1,4-butanediol and 2-methyl-1,3 propanediol, respectively.

Figure 2:
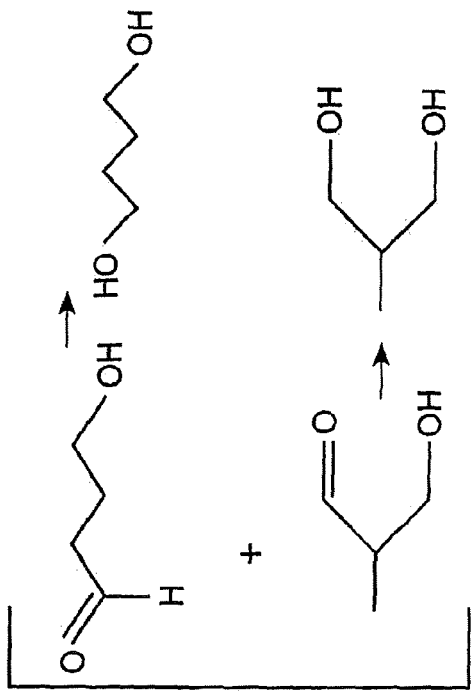
FIG. 2 depicts the conversions accomplished in an alternate process embodiment of the present invention.

Alternatively, as shown in FIG. 2, glycerol may be selectively converted to allyl alcohol essentially directly, and the allyl alcohol thus formed may be recovered and hydroformylated as just described. As related in WO 2008/092115 A1 (the Regents of the University of California, applicant), published Jul. 31, 2008, there had been a number of early research publications from decades earlier which described the synthesis of allyl alcohol from the reaction of glycerol with organic acids. The known methods were characterized as "not very adequate", however, and the '115 application concerns an improved method of synthesis of allyl alcohol from glycerol wherein a yield of 80% or greater is reported. In the process of the 115 application, glycerol is combined with formic acid in a reaction mixture, the reaction mixture is heated under an inert atmosphere to between 230 and 240 degrees Celsius, and allyl alcohol is recovered from the reaction mixture by distillation. Unconverted glycerol could be recycled for reaction with additional formic acid, while allyl formate formed as a byproduct could be hydrolyzed to the desired allyl alcohol product with sodium hydroxide. According to the '115 application, the charring and inadequate yield characterizing the prior efforts were due to the presence of oxygen during the synthesis, leading to an oxidative decomposition of the glycerol feedstock. A different approach to improving the glycerol-organic acid synthesis is shown in BR 8904178, published Feb. 13, 1991, wherein a mixture of glycerol, oxalic and formic acids was microwave (2.45 GHz) irradiated to reportedly yield allyl alcohol in 60 percent yields.

Other routes have been proposed as well for converting glycerol to allyl alcohol but which do not involve a reaction with an organic acid. For example, in the context of producing acrylic acid from glycerol via allyl alcohol, a catalytic gas phase process is proposed in JP 2008162907 whereby a solid catalyst containing at least one of iron, vanadium and molybdenum is used to convert glycerol to an intermediate product mixture including allyl alcohol, and then this intermediate product mixture undergoes a gas phase oxidation in the presence of a molybdenum-vanadium catalyst to produce acrylic acid. An alternative proposed by Liu et at in *Chemical Communications*, vol. 46, no. 8, pp. 1238-1240 (2010) involves converting glycerol to allyl alcohol in the presence of a high surface area iron oxide catalyst mixed with quartz, through a combination of dehydration and consecutive hydrogen transfer. Yet another alternative proposed in DE 102008031828 A1 (published Jan. 7, 2010) produces allyl alcohol from glycerol in a gas phase process in the presence of a heterogeneous catalyst based on tungsten and molybdenum. Finally, Cook et al., in *Journal of the American Chemical Society*, vol. 118, no. 39, pp. 9448-9449 (1996), describe the deoxydehydration of diols and polyols including glycerol to yield alkenes and allylic alcohols in the presence of a metal oxo triphenylphosphine complex.

Following the synthesis and recovery of allyl alcohol according to a method such as has been described herein, then in the alternate embodiment of FIG. 2 as in FIG. 1, the allyl alcohol is hydroformylated to provide 4-hydroxybutyraldehyde and 3-hydroxy-2 methylpropionaldehyde. These are then independently or, preferably, collectively hydrogenated to yield 1,4-butanediol and 2-methyl-1,3 propanediol.

Hydroformylation is well known in the art as a catalytic method for the conversion of an olefin into an aldehyde product having one carbon more than the starting olefin, by the addition of one molecule each of hydrogen and carbon monoxide to the carbon-carbon double bond. If the organic substrate contains more than one carbon-carbon double bond, more than one formyl group can be added to the substrate, thereby increasing the number of carbon atoms contained in the product molecule by more than one.

The hydroformylation process of the present invention is addressed in preferred embodiments to the hydroformylation of allyl alcohol as the olefin, and in one aspect seeks to make use of compressed gas-expanded liquids, building on the discoveries described in U.S. Pat. No. 7,365,234 to Subramaniam et al.

By way of background and context, such compressed gas-expanded liquids (CGXLs) may be understood as a continuum of compressible media generated when various amounts of a compressed dense phase gas are added to a liquid to be expanded. As briefly mentioned above, CGXLs provide a number of benefits in the context of carrying out certain chemical conversions such as the contemplated hydroformylation of biobased allyl alcohol. Near-critical fluids—defined for purposes of this patent application as pure fluids or fluid mixtures that are between 0.7-1.3 times their absolute critical temperatures—possess highly tunable transport properties ranging from gas-like diffusivities to liquid-like viscosities. See Subramaniam et al., *Reaction in supercritical fluids—a review*, Industrial & Engineering Chemistry Process Design and Development, 25 1-12 (1986). In CGXLs, non-dissolving gases provide a similar degree of "tunability", in that the solubilities of many gaseous reagents (i.e., $O_2$, $H_2$) in CGXLs are enhanced several-fold but also to varying degrees, relative to a neat, unexpanded liquid phase. See Hert et al., *Enhancement of oxygen and methane solubility in 1-hexyl-3-methylimidazolium bis(trifluoromethylsulfonyl)imide using carbon dioxide*, Chemical Communications, 2603-2605 (2005); Wei et al., *Autoxidation of 2,6-ditertbutyl-phenol with cobalt Schiff base catalysts by oxygen in $CO_2$-expanded liquids*, Green Chemistry, 6 387-393 (2004); Solinas et al., *Enantioselective hydrogenation of imines in ionic liquid/carbon dioxide media*, Journal of American Chemical Society, 126 16142-16147 (2004); Bezanehtak et al., *Vapor-liquid equilibrium for the carbon dioxide+hydrogen+methanol ternary system*, Journal of Chemical Engineering Data, 49 430-434 (2004); Xie et al., *Bubble and dew point measurements of the ternary system carbon dioxide+methanol+hydrogen at 313.2 K*, Journal of Chemical Engineering Data, 50 780-783 (2005).

Importantly, in the context of the present invention wherein a dense petroleum gas such as propane or butane is supplied to volumetrically expand the allyl alcohol substrate at near critical conditions, due to the very high expansion capabilities afforded by dense propane (providing about a ten-fold increase in volume in the examples below), the amount of hydrogen that can be dissolved into the liquid phase for reaction with the allyl alcohol is very substantially increased and to a greater extent than is true of the carbon monoxide reactant, so that hydrogen:carbon monoxide ratios approaching 1:1 may be realized in the liquid phase—very nearly the ratio found in the gas phase, in the supply of synthesis gas as may be secured through the gasification of biomass. By comparison, we found that hydrogen:carbon monoxide ratios of no more than about 0.6:1 could be realized using carbon dioxide-expanded toluene and allyl alcohol in keeping with the prior '234 Subramaniam patent's teachings.

While the reactant gases may be more fully and readily dissolved in the expanded liquid phase in both the '234 patent and in the present inventive process, enabling increased rates of reaction and milder conditions to be used generally, the higher hydrogen to carbon monoxide ratios made possible by the present invention are desirable for avoiding an inhibitory effect with higher amounts of carbon monoxide and for tuning the process to achieve a desired product regioselectivity, under milder conditions and at lower system pressures.

Thus, in the preferred application to the hydroformylation of allyl alcohol, a product ratio of the linear, n-aldehyde HBA to the branched, iso-aldehyde HMPA of about 3 to 1, more preferably about 8 to 1, and most preferably about 10 to 1 will be possible, with a targeted chemoselectivity preferably greater than about 70%, more preferably greater than about 80%, and most preferably greater than about 90%. As used herein, the term "chemoselectivity" or "$S_a$" refers to the moles of aldehydes or the allyl alcohol isomers (e.g., propionaldehyde) or hydrogenated derivatives (e.g., propanol) formed relative to the moles of substrate (e.g., allyl alcohol) converted during the hydroformylation process.

In one aspect, the dense propane preferably has a volume fraction in the liquid phase between 5% and 98%. In another aspect, more than 50% of the liquid phase volume is preferably replaced with the dense propane, more preferably replacing about 80% or more and most preferably about 95% or more of the liquid phase volume.

In still another aspect, the reaction occurs at relatively mild temperatures and pressures. Generally, temperatures of about 80 degrees Celsius or less and especially 70 deg. C. or less are contemplated, with pressures overall from about 5 MPa and lower and especially about 4 MPa and lower. Typical temperatures range between 50° C. and 70° C., and typical pressures are less than 5 MPa, with pressures between about 3 to 4 MPa being exemplary. Within these general overall system temperatures and pressures, however, it should be noted that product regioselectivities (where "regioselectivity" or "n/i" refers to the ratio of linear to branched aldehydes in the hydroformylation product composition) and chemoselectivities can vary based on the pressures of syngas used versus of the dense gas serving both as a liquid expansion medium and as a solvent/diluent for the substrate and catalyst, and further based on the overall concentration or amount of the substrate supplied to be hydroformylated.

Thus, for example, we have found that for a first given quantity of allyl alcohol and the pressure of supplied propane for achieving the approximately ten-fold volumetric expansion mentioned above (namely, about 2.6 MPa (26 atmospheres) at 70 degrees Celsius), at complete conversion of allyl alcohol, a syngas pressure of 4.5 MPa (45 atmospheres) provided an HBA:HMPA product ratio of about 5.6:1 and a reaction time to completion of about 1.67 hours, while a syngas pressure of 3.5 MPa (35 atmospheres) after about 4.5 hours yielded an HBA:HMPA ratio of 8.45:1, and a syngas pressure of 2.5 MPa (25 atmospheres) gave an HBA:HMPA ratio of in excess of 10.9:1 with no increase in the reaction time, but a reduced chemoselectivity to the aldehyde products in combination. For a second, lesser quantity of the allyl alcohol substrate and given the same pressure of supplied propane with the same catalyst, reaction vessel and temperature, by comparison, the chemoselectivity to the aldehydes was maintained while a substantial improvement in the HBA:HMPA ratio was realized in going from 4.5 MPa (45 atmospheres) of supplied syngas (HBA:HMPA ratio of 4.7:1) to 3.5 MP (35 atmospheres) and less (HBA:HMPA ratio of more than 10:1) of supplied syngas. Reaction times to completion varied only slightly in going from 4.5 MPa (45 atmospheres) supplied syngas to 3.5 MPa (35 atmospheres) and less.

These results (and the examples below) demonstrate a further useful aspect of the present invention, in that under complete conversion conditions and under steady-state conditions with selected constant pressure supplies of propane and of syngas, one may by adjusting the amount of allyl alcohol supplied in a continuous hydroformylation process alter the selectivities and thus yields of the linear and branched aldehyde products, as desired. In the majority of instances, since it is expected that most producers will seek to maximize production of the linear aldehyde HBA and its derivative downstream products (e.g., 1,4-butanediol), this will mean limiting the concentration of the allyl alcohol substrate in the process as necessary to achieve a high HBA:HMPA product ratio.

In one embodiment, the hydroformylation process is carried out in a homogeneous reaction system wherein dense propane acts both as an expansion medium for allyl alcohol but as a solvent/diluent for the allyl alcohol and for a transition metal-, preferably rhodium-based, hydroformylation catalyst, and syngas is supplied for reaction with the allyl alcohol in the liquid phase. Since allyl alcohol and dense propane are substantially completely miscible under the contemplated reaction conditions, the process may preferably be conducted in the substantial absence of any other added solvent. Further, as will be understood by reference to the schematic embodiment 10 of the inventive process shown in FIG. 3, since propane readily transitions from a gaseous condition under standard conditions to a liquid and vice-versa, as allyl alcohol, carbon monoxide and hydrogen are provided to a reactor 12 in the form of allyl alcohol stream 14 and synthesis gas stream 16 and caused to react therein in the presence of a hydroformylation catalyst, solvent removal and recovery from the hydroformylation product stream 18 preferably involves merely degassing the hydroformylation product in a simple vapor-liquid separator 20. The propane 22 degassing from the hydroformylation product 18 is taken overhead to be recompressed in step 24 and supplied to the reactor 12 as propane recycle stream 26, while the degassed hydroformylation product stream 28 is reacted with hydrogen 30 in a hydrogenation step 32, to produce a 1,4-butanediol product 34 and a 2-methyl-1,3 propanediol product 36. Makeup propane, if needed, is supplied to the hydroformylation reactor 12, via stream 38.

With respect to the hydrogenation step 32, various catalysts and methods will be familiar to those skilled in the art for accomplishing this step. For example, a bimetallic catalyst and process are described in U.S. Pat. No. 5,874,652 to Pitchai et al., and other references are noted. More recently, U.S. Pat. No. 6,969,780 to Dubner et al. describes an improved fixed bed process as well as other catalysts and methods that have been commercially practiced or investigated over time. While the HBA and HMPA products might in one embodiment be separated before being hydrogenated individually, preferably the mixed aldehyde products will be hydrogenated in a single feed, and the 1,4-butanediol and 2-methyl-1,3 propanediol products separated by distillation or by simulated moving bed chromatography.

It will be noted that the embodiment 10 of FIG. 3 does not show a catalyst recovery step for separating out and recovering catalyst from the hydroformylation product stream 18. Those skilled in the art will appreciate, however, that if the stream 18 contains some hydroformylation catalyst from the reactor 12—for example, catalyst dissolved in the propane in stream 18 prior to the degassing step 20—then the embodiment 10 should also include a catalyst removal and recycle loop. Preferably, as will be described in greater detail hereafter, the catalyst will be retained substantially completely within the reactor 12 and not carried over into the hydroformylation product stream 18.

The hydroformylation catalyst used in reactor 12 will comprise a transition metal capable of catalyzing the hydroformylation of an olefinic feed such as allyl alcohol, and may additionally contain labile ligands which are either displaced during the catalytic reaction, or take an active part in the catalytic transformation. The preferred transition metals are those comprising Group 8 of the Periodic Table. The preferred metals for hydroformylation are rhodium, cobalt, iridium, ruthenium, palladium, and platinum. The Group 8 metal is preferably rhodium. The amount of rhodium in the liquid reaction mixture can vary, but is generally from 10 to 500 ppm by weight, preferably from 30 to 350 ppm by weight and particularly preferably from 50 to 300 ppm by weight.

Group 8 catalysts suitable for hydroformylation, can be prepared or generated according to techniques well known in the art, as described, for example, in WO 95 30680, U.S. Pat. No. 3,907,847; and J. Amer. Chem. Soc., 115, 2066 (1993). Suitable Group 8 metal compounds are hydrides, halides, organic acid salts, acetylacetonates, inorganic acid salts, oxides, carbonyl compounds and amine compounds of these metals. Preferred salts include, for example, rhodium salts such as rhodium acetate, rhodium chloride or rhodium nitrate, rhodium complexes such as rhodium acetylacetonate and/or rhodium carbonyl compounds. In addition, the catalyst may be achiral or chiral.

The ligands can be monodentate or polydentate, and in the case of chiral ligands, either the racemate or one enantiomer or diastereomer can be used. Preferred ligands are ligands which contain nitrogen, phosphorus, arsenic, or antimony as donor atoms; particular preference is given to phosphorus-containing ligands, such as phosphines, phosphine oxides, phosphinanes, phosphinines, phosphinites, phosphites, and phosphonites.

Examples of phosphines are triphenylphosphine, tris(p-tolyl)phosphine, tris(m-tolyl)phosphine, tris(o-tolyl)phosphine, tris(p-methoxyphenyl)phosphine, tris(p-fluorophenyl)phosphine, tris(p-chlorophenyl)phosphine, tris(p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl)phosphine, tri-2-furylphosphine, tribenzylphosphine, benzyldiphenylphosphine, tri-n-butylphosphine, tri-1-butylphosphine, tri-t-butylphosphine, bis(2-methoxyphenyl)phenylphosphine, neomenthyldiphenylphosphine, 1,2-bis(dicyclohexylphosphino)ethane, bis(dicyclohexylphosphino)methane, 1,2-bis(diethylphosphino)ethane, 1,2-bis(2,5-diethylphospholano)benzene [Et-DUPHOS], 1,2-bis(2,5-diethylphospholano)ethane [Et-BPE], 1,2-bis(dimethylphosphino)ethane, bis(dimethylphosphino)methane, 1,2-bis(2,5-dimethylphospholano)benzene [Me-DUPHOS], 1,2-bis(2,5-dimethylphospholano)ethane [Me-BPE], 1,2-bis(diphenylphosphino)benzene, 2,3-bis(diphenylphosphino)bicyclo[2.2.1]hept-5-ene [NORPHOS], 2,2'-bis(diphenylphosphino)-1,1'-binaphthyl [BINAP], 2,2'-bis(diphenylphosphino)-1,1'-biphenyl [BISBI], 2,3-bis(diphenylphosphino)butane, 1,4-bis(diphenylphosphino)butane, 1,2-bis(diphenylphosphino)ethane, bis(2-diphenylphosphinoethyl)phenylphosphine, 1,1'-bis(diphenylphosphino)ferrocene, bis(diphenylphosphino)methane, 1,2-bis(diphenylphosphino)propane, 2,2'-bis(di-p-tolylphosphino)-1,1'-binaphthyl, O-isopropylidene-2,3-dihydroxy-1,4-bis(diphenylphosphino)butane [DIOP], 2-(diphenylphosphino)-2'-methoxy-1,1'-binaphthyl, 1-(2-diphenylphosphino-1-naphthyl)isoquinoline, 1,1,1-tris(diphenylphosphino)ethane, and/or tris(hydroxypropyl)phosphine.

Examples of phosphinanes include 2,6-bis(2,4-dimethylphenyl)-1-octyl-4-phenylphosphinane, 1-octyl-2,4,6-triphenylphosphinane and further ligands described in WO 02/00669.

Examples of phosphinines include 2,6-dimethyl-4-phenylphosphinine, 2,6-bis(2,4-dimethylphenyl)-4-phenylphosphinine and also further ligands described in WO 00/55164.

Examples of phosphites are trimethyl phosphite, triethyl phosphite, tri-n-propyl phosphite, tri-1-propyl phosphite, tri-n-butyl phosphite, tri-1-butyl phosphite, tri-t-butyl phosphite, tris(2-ethylhexyl)phosphite, triphenyl phosphite, tris(2,4-di-t-butylphenyl)phosphite, tris(2-t-butyl-4-methoxyphenyl) phosphite, tris(2-t-butyl-4-methylphenyl)phosphite, tris(p-cresyl)phosphite. Further examples are sterically hindered phosphite ligands as are described, inter alia, in EP 155 508; U.S. Pat. No. 4,668,651; U.S. Pat. No. 4,748,261; U.S. Pat. No. 4,769,498; U.S. Pat. No. 4,774,361; U.S. Pat. No. 4,835,299; U.S. Pat. No. 4,885,401; U.S. Pat. No. 5,059,710; U.S. Pat. No. 5,113,022; U.S. Pat. No. 5,179,055; U.S. Pat. No. 5,260,491; U.S. Pat. No. 5,264,616; U.S. Pat. No. 5,288,918; U.S. Pat. No. 5,360,938; EP 472 071; EP 518 241; and WO 97/20795. Triphenyl phosphites which are substituted by 1 or 2 isopropyl and/or tert-butyl groups on the phenyl rings, preferably in the ortho position relative to the phosphite ester group, are preferably used. Bisphosphite ligands which are described, inter alia, in EP 1 099 677; EP 1 099 678; WO 02.00670; JP 10279587; EP 472017; WO 01/21627; WO 97/40001; WO 97/40002; U.S. Pat. No. 4,769,498; EP 213639; and EP 214622, are particularly preferably used.

Customary phosphinite ligands are described, inter alia, in U.S. Pat. No. 5,710,344; WO 95 06627; U.S. Pat. No. 5,360, 938; and JP 07082281. Examples are diphenyl(phenoxy) phosphine and its derivatives in which all or some of the hydrogen atoms are replaced by alkyl or aryl radicals or halogen atoms, diphenyl(methoxy)phosphine, diphenyl (ethoxy)phosphine, etc.

Examples of phosphonites are methyldiethoxyphosphine, phenyldimethoxyphosphine, phenyldiphenoxyphosphine, 6-phenoxy-6H-dibenz[c,e][1,2]oxaphosphorin and their derivatives in which all or some of the hydrogen atoms are replaced by alkyl or aryl radicals or halogen atoms and ligands as described in WO 98/43935; JP 09-268152; and DE 198 10 794, and in the German patent applications DE 199 54 721 and DE 199 54 510.

Other examples of rhodium catalysts include $RhCl_3$, $Rh(NO_3)_3$, $Rh(OAc)_3$, $Rh_2O_3$, $Rh(acac)(CO)_2$, $[Rh(OAc)(CON)]_2$, $Rh_4(CO)_{12}$, $Rh_6(CO)_{16}$, $RhH(CO)(Ph_3P)_3$, $[Rh(OAc)(CO)_2]$, $[RhCl(COD)]_2$, $Rh(CO)_2(acac)$, $Rh(CO)_2(C_4H_9COCHCO-t-C_4H_9)$, $Rh_2O_3$, $Rh(O_2CCH_3)_2$, and $Rh(2$-ethylhexanoate), wherein "acac" is an acetylacetonate group; "OAc" is an acetyl group; "COD" is 1,5-cyclooctadiene; "Ph" is a phenyl group, and "OAr" is 2,4-di-tertbutyl-phenyl. However, it should be noted that the Group 8 metal compounds are not necessarily limited to the above listed compounds. Rhodium compounds that contain ligands which can be displaced by the multidentate phosphites are a preferred source of rhodium.

Because rhodium in particular is quite costly in comparison to other transition metals which have been investigated for use in hydroformylation, various efforts have been undertaken in the art to develop catalysts and methods whereby rhodium losses to leaching and the like may be minimized and catalysts recovered for reuse. Any of the catalysts and methods described below may be contemplated for the present invention, provided some provision is made to either substantially retain the catalyst in the reactor 12 and prevent any substantial loss of rhodium in the hydroformylation products stream 18, or recover substantially all of the rhodium value in the stream 18 for recycle and reuse in the reactor 12.

Several approaches for catalyst recovery have been reported in the literature. The first approach involves employing a "phase transition switch" whereby reactions are performed homogeneously, following which the catalysts are recovered from the product stream via phase transition triggered by a change in either the system temperature (see Horvath et al., *Facile catalyst separation without water: fluorous biphasic hydroformylation of olefins*, Science 266 (5182) 72-75 (1994); Zheng et al., *Thermoregulated phase transfer ligands and catalysis. III. Aqueous/organic two-phase hydroformylation of higher olefins by thermoregulated phase-transfer catalysis*, Catalysis Today 44 175-182 (1998)) or pressure (see Koch et al., *Rhodium-catalyzed hydroformylation in supercritical carbon dioxide*, Journal of American Chemical Society 120 13398-13404 (1998); Palo et al., *Effect of ligand modification on rhodium-catalyzed homogeneous hydroformylation in supercritical carbon dioxide*, Organometallics 19 81-86 (2000)).

Another involves immobilizing homogeneous rhodium ("Rh") catalysts on various supports to form a heterogenized homogeneous catalyst that can be easily applied in fixed bed or slurry type reactors, i.e., the silicate MCM-41 (see Marteel et al., *Supported platinum/tin complexes as catalysts for hydroformylation of 1-hexene in supercritical carbon dioxide*, Catalysis Communications 4 309-314 (2003)), zeolites (see Mukhopadhyay et al., *Encapsulated HRh(CO)— $(PPh_3)_3$ in microporous and mesoporous supports: novel heterogeneous catalysts for hydroformylation*, Chemical Materials 15 1766-1777 (2003)), nanotubes (see Yoon et al., *Rh-based olefin hydroformylation catalysts and the change of their catalytic activity depending on the size of immobilizing supporters*, Inorganica Chimica Acta. 345 228-234 (2003)), supported aqueous phase catalysis ("SAPC") (see Dessoudeix et al., *Apatitic tricalcium phosphate as novel smart solids for supported aqueous phase catalysis (SAPC)*, Advanced Synthetic Catalysis 344 406-412 (2002)), polymers (see Lu et al., *Hydroformylation reactions with recyclable rhodium complexed dendrimers on a resin*, Journal of American Chemical Society 125 13126-13131 (2003) and Lopez et at, *Evaluation of polymer-supported rhodium catalysts in 1-octene hydroformylation in supercritical carbon dioxide*, Industrial & Engineering Chemistry Research 42 3893-3899 (2003)), and smectite, especially montmorillonite, clays wherein the rhodium or other transition metal catalyst is intercalated into the clay (see Lee and Alper, *Regioselective hydroformylation of allyl acetates catalyzed by rhodium-montmorillonite*, Journal of Molecular Catalysis A: Chemical, vol. 111, pp 17-23 (1996); Valli and Alper, *Organorhodium Complex on Smectite Clay: Preparation, Characterization, and Catalytic Activity for the Hydroformylation of Vinylsilanes*, Chemistry of Materials, vol. 7, pp. 359-362 (1995); and, Farzaneh and Pinnavaia, *Metal Complex Catalysts Interlayered in Smectite Clay. Hydroformylation of 1-Hexene with Rhodium Complexes Ion Exchanged into Hectorite*, Inorganic Chemistry, vol. 22, no. 15, pp. 2216-2220 (1983)).

Previously, several research groups have developed polystyrene supports that facilitate the recycle of rhodium catalysts. Uozumi et al., *VII-B-1 Amphiphilic Resin-Supported Rhodium-Phosphine Catalysts for C—C Bond Forming Reactions in Water*, Synth. Catal. 344 274 (2002); Otomaru et al., *Preparation of an Amphiphilic Resin-Supported BINAP Ligand and Its Use for Rhodium-Catalyzed Asymmetric 1,4-Addition of Phenylboronic Acid in Water*, Org. Lett. 6 3357 (2004); Miao et al., *Ionic Liquid-Assisted Immobilization of Rh on Attapulgite and Its Application in Cyclohexene Hydrogenation*, J. Phys. Chem. C 111, 2185-2190 (2007); Grubbs et al., *Catalytic reduction of olefins with a polymer-supported rhodium(I) catalyst*, J. Am. Chem. Soc. 93 3062-3063 (1971); Nozaki et al., *Asymmetric Hydroformylation of Olefins in a Highly Cross-Linked Polymer Matrix*, J. Am. Chem. Soc. 120 4051-4052 (1998); Nozaki et al., *Asymmetric Hydroformylation of Olefins in Highly Crosslinked Polymer Matrixes*, Bull. Chem. Soc. Jpn. 72 1911-1918 (1999); Shibahara et al., *Solvent-Free Asymmetric Olefin Hydroformylation Catalyzed by Highly Cross-Linked Polystyrene-Supported (R,S)-BINA-PHOS-Rh(I) Complex*, J. Am. Chem. Soc. 125 8555-8560 (2003). However, the typical polymer supports suffer from serious limitations like insolubility, gel formation, tedious procedures to swell the polymer, and limited loading of the phosphorus ligand in the polymer backbone (e.g., 0.17 mmol/g). Many of these issues relate to the fact that polymers that are purchased commercially, or are prepared by conventional radical polymerization of styrene, have high molecular weight and/or broad molecular weight distribution. Thus, they have poor solubility properties. The slower kinetics of reactions catalyzed by gel-phase or solid-phase catalysts have important practical effects as well. For instance, the conjugate addition of arylboronic acids to enones suffers from competing hydrolysis of the costly boronic acids; the slower the catalyst is, the more hydrolysis occurs. Thus, when a heterogeneous polystyrene-supported catalyst is used for the conjugate addition, a 4-5-fold excess of boronic acid is required.

In commonly-assigned WO2010/057099A1, soluble polymer-supported rhodium catalysts that have a narrow molecular weight distribution were prepared which can be readily recycled by precipitation and filtration. In addition to molecular weight control, it was important to design a polymer support that could bind Rh in a multidentate fashion. Such binding was expected to better site-isolate the rhodium catalysts as well as prevent leaching of rhodium from the polymer.

The catalyst composition described therein comprises a polymer functionalized with a multidentate ligand for binding a transition metal containing compound. The functionalized polymer forms a transition metal complex with the transition metal. In one aspect, the functionalized polymer has a number average molecular weight of about 5,000 to 30,000 g/mol and a polydispersity index of about 1.0 to 2.0. In another aspect, the functionalized polymer has a number average molecular weight of about 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000 g/mol, or some range therebetween. For example, the functionalized polymer may have a number average molecular weight selected from a range consisting of about 6,000 to 25,000 g/mol, 7,000 to 20,000 g/mol, 8,000 to 15,000 g/mol, and 9,000 to 12,000 g/mol. In still another aspect, the polydispersity index is about 1.0, 1.1, 1.2, 1.3, 1.4, 1.5, 1.6, 1.7, 1.8, 1.9, 2.0, or some range therebetween. The preferred catalyst composition comprises polystyrene-co-6,6'-(3,3'-di-tert-butyl-5,5'-divinylbiphenyl-2,2' diyl)bis(oxy)didibenzo[1,3,2]dioxaphosphepine.

In another aspect, the functionalized polymer is selected from the group consisting of polystyrene, polyethylene glycol, poly(vinylpyrrolidine), poly(ethylene oxide), poly(vinyl chloride), polyethylenimine, polyacrylonitrile, poly(ethyleniminodiacetic acid), polyphazene, polysiloxanes, polyacrylamide, or a dendrimeric polymer, including block or copolymers thereof. The functional groups may be attached to the polymer chain by copolymerization with one or more monomers (e.g. compound (5) in Example 1 of the WO '099 application and styrene as described herein). Alternatively, the functionalized polymer may be prepared by functionalizing the already formed polymer, for example as shown in Bergbreiter, *Using Soluble Polymers to Recover Catalysts and Ligands*, Chem. Rev. 102(10), 3345-3384 (2002), which was incorporated by reference in the prior WO '099 application. The functionalized polymer may be cross-linked or uncrosslinked. In one aspect, the polymer is cross-linked and has a crosslinker ratio ranging from 8 to 12 in moles of monomer to moles of crosslinking monomer. Exemplary classes of polymer backbones are disclosed in Bergbreiter.

In one aspect, the functionalized polymer, such as polystyrene, preferably has at least one moiety selected from the group consisting of amino, epoxy, carboxylic acid, carboxylic ester, ortho ester, anhydride, carbon-carbon double bond, phosphine, phosphite, and pyridyl. In another aspect, functionalized polymer is selected from the group consisting of a copolymer of polystyrene or polyethylene glycol, and the ligand comprises a phosphine, phosphinane, phosphinine, phosphinite, phosphite, or phosphonite moiety. An exemplary functionalized polymer includes a phosphite-based bidentate ligand. The bis(phosphate) functionalized polymer ligand is able to sequester the transition metal (rhodium) with two phosphites.

In another aspect, the catalyst composition has a transition metal complex which is covalently bound or chelated to said polystyrene at a ratio of about 1:10 to 1:20 mol:mol in terms of mole metal to mole of styrene monomer.

In another aspect, transition metal of said transition metal complex is selected from the group consisting of rhodium, cobalt, iridium, ruthenium, nickel, palladium, and platinum.

In another aspect, the catalyst composition comprising the polymer functionalized with a multidentate ligand is retained and reused through filtration. The filtration step may be performed either batchwise or continuously. Total losses of the transition metal are preferably less than 10%, still more preferably less than 5%, and are most preferably less than 2%.

In one embodiment, the catalyst composition is in the form of bulky polymer-supported catalyst complexes of transition metals (such as Rh) such that the bulky complexes are substantially retained in the retentate composition, and the leakage of Rh and other metals through a suitable nanofiltration membrane into the permeate composition is lowered to less than 100 parts per billion, preferably less than 50 parts per billion and more preferably less than 30 parts per billion. Filtration rates are helped by the reduction in liquid viscosity that accompanies compressed gas expansion and the pressure contribution of the dense propane gas.

The preferred nanofiltration membranes in the WO '099 filing have a molecular weight cut-off range selected from the group consisting of 100 to 1000 g/mol, 150 to 600 g/mol, or 200 to 500 g/mol based on 90% rejection of the solute. Several membranes have been claimed to be capable of nanofiltration in organic solvent, known as solvent resistant nanofiltration (SRNF) membranes. Koch SelRO® membrane systems (USA) are solvent-stable, commercially available, and supplied in a wet form. Among of the most popularly examined membranes (MPF-60, MPF-44 and MPF-50), MPF-50 has been the most studied commercial SRNF membrane in many applications. STARMEM® from Membrane Extraction Technology (United Kingdom) and Solsep membranes from SolSep BV-Robust Membrane Technologies (The Netherlands) appeared in the market recently and have been successfully demonstrated in the literature for organic solvent nanofiltration. Another series of membranes, Desal-5 and Desal-5-DK from GE Osmonics (USA) are designed for aqueous applications, but are also selective in SRNF. Vandezande et al., *Solvent resistant nanofiltration: separating on a molecular level*, Chemical Society Reviews 37 (2) 365-405 (2008) summarized more membrane information.

The membrane nanofiltration setups described in the literature can be categorized into two groups according to the flow direction relative to the membrane surface: dead-end filter (perpendicular) and cross-flow filter (parallel). Commercially available dead-end filtration cells include: a solvent-resistant stirred cell from Millipore (USA), MET cell from Membrane Extraction Technology Ltd. (UK) and HP4750 stirred cell from Sterlitech Corporation (USA). However, an alternative setup GE Sepa™ CF II Med/High foulant allows for cross-flow filtration with any membrane. Cross-flow filtration set-ups are described in Nair et al., *Increased catalytic productivity for nanofiltration-coupled Heck reactions using highly stable catalyst systems*, Green Chemistry 4(4) 3 19-324 (2002); Patterson et al., *Membrane selectivity in the organic solvent nanofiltration of trialkylamine bases*, Desalination 218 (1-3) 248-256 (2008); Roengpithya et al., *Towards a continuous dynamic kinetic resolution of 1-phenylethylamine using a membrane assisted, two vessel process*, Chemical Communications (33) 3462-3463 (2007); Peeva et al., *Effect of concentration polarisation and osmotic pressure on flux in organic solvent nanofiltration*, Journal of Membrane Science 236 (1-2), 12 1-136 (2004).

The present invention is more readily appreciated by a consideration of the following, non-limiting examples:

EXAMPLE 1

2.439 g ($4.2 \times 10^{-2}$ moles) of allyl alcohol, and 0.045 g ($4.88 \times 10^{-5}$ moles) of $HRh(CO)(PPh_3)_3$ were taken in a 100 mL Hastelloy C Parr reactor and sealed. The contents were then flushed three times each with nitrogen, propane and syngas at ambient temperature. After complete degassing of the contents, the reactor was heated to reach the desired temperature of 70° C. After the temperature was attained, propane was fed into the reactor by a pump to the desired pressure of 2.6 MPa (26 atm) at 70° C. This was allowed to equilibrate for at least 15 minutes, with agitation at 200 rpm. Necessary refilling of the propane was made if the pressure went below 2.6 MPa at 70° C. The mixture was allowed to equilibrate for 15 minutes every time propane was fed into the reactor. After stabilization (observation of a constant pressure at 70° C.), syngas ($H_2:CO=-1:1$) was introduced from a pressurized reservoir into the reactor via a non-return valve with a constant pressure regulator at 3.6 MPa (36 atm), so that a constant pressure of syngas of 1.0 MPa (10 atm) is maintained inside the reactor. The reaction was started immediately by switching on the agitation at 900-1000 rpm. The consumption of the syngas was monitored by a pressure transducer attached to the reservoir maintained at ambient temperature. The consumption of the syngas (depletion of reservoir pressure) was followed online and the reaction was continued till the depletion of syngas from the reservoir became minimal. At that point the syngas feed was discontinued, and reaction was stopped by shutting down the agitation. The reactor was allowed to cool to ambient temperature naturally. After cooling to ambient temperature, the gases were exhausted from the reactor through a cold trap to capture any escaping volatile matter. The contents of the reactor were then collected for necessary analytical processing. 100% Allyl alcohol conversion was observed along with a high 93.6 chemoselectivity to the aldehyde products, and n/iso ratio 10.3 was obtained. Overall TOF was calculated as 1145 $h^{-1}$ at this conversion, where "TOF" or "turnover frequency" is conventionally understood to refer to the moles of substrate converted (to all products) per mole of catalyst per hour during fixed-time batch runs.

EXAMPLE 2

2.477 g ($4.264 \times 10^{-2}$ moles) of allyl alcohol, and 0.046 g ($5.05 \times 10^{-5}$ moles) of $HRh(CO)(PPh_3)_3$ were taken in the 100 mL Hastelloy C Parr reactor and sealed. The contents were then flushed three times each with nitrogen, propane and syngas at ambient temperature. After the stabilization on addition of 2.6 MPa (26 atm) propane at 70° C. as described in Example 1, syngas ($H_2:CO=1:1$) was introduced and the reactor pressure was maintained at 51 atm, so as to have a constant syngas pressure of 2.5 MPa (25 atm) inside the reactor. The reaction was followed up in the same way as described in Example 1. 100% Allyl alcohol conversion was observed along with a 93.10% chemoselectivity to the aldehyde products, and n/iso ratio 10.23 was obtained. Overall TOF was calculated as 1125 $h^{-1}$ at this conversion.

EXAMPLE 3

2.517 g ($4.33 \times 10^{-2}$ moles) of allyl alcohol, and 0.045 g ($4.97 \times 10^{-5}$ moles) of $HRh(CO)(PPh_3)_3$ were taken in the 100 mL Hastelloy C Parr reactor and sealed. The contents were then flushed three times each with nitrogen, propane and syngas at ambient temperature. After the stabilization on addition of 2.6 MPa (26 atm) propane at 70° C. as described in Example 1, syngas ($H_2:CO=1:1$) was introduced and the reactor pressure was maintained at 6.1 MPa (61 atm), so as to have a constant syngas pressure of 3.5 MPa (35 atm) inside the reactor. The reaction was followed up in the same way as described in Example 1. 100% Allyl alcohol conversion was observed along with a 93.17% chemoselectivity to the aldehyde products, and n/iso ratio 10.4 was obtained. Overall TOF was calculated as $1306 \times 10^{-1}$ at this conversion.

EXAMPLE 4

9.562 g ($1.646 \times 10^{-1}$ moles) of allyl alcohol, and 0.046 g ($5.007 \times 10^{-5}$ moles) of $HRh(CO)(PPh_3)_3$ were taken in the 100 mL Hastelloy C Parr reactor and sealed. The contents were then flushed three times each with nitrogen, propane and syngas at ambient temperature. After the stabilization on addition of 2.6 MPa (26 atm) propane at 70° C. as described in Example 1, syngas ($H_2:CO=1:1$) was introduced and the reactor pressure was maintained at 6.1 MPa (61 atm), so as to have a constant syngas pressure of 3.5 MPa (35 atm) inside the reactor. The reaction was followed up in the same way as described in Example 1. 30% Ally) alcohol conversion was observed along with a 85.8% chemoselectivity to the aldehyde products, and n/iso ratio 8.45 was obtained. Overall TOF was calculated as 184 $h^{-1}$ at this conversion in 5 h.

EXAMPLE 5

2.457 g ($4.23 \times 10^{-2}$ moles) of allyl alcohol, and 0.0454 g ($4.941 \times 10^{-5}$ moles) of $HRh(CO)(PPh_3)_3$ were taken in the 100 mL Hastelloy C Parr reactor and sealed. The contents were then flushed three times each with nitrogen, propane and syngas at ambient temperature. After the stabilization on addition of 2.6 MPa (26 atm) propane at 70° C. as described in Example 1, syngas ($H_2:CO=2:1$) was introduced and the reactor pressure was maintained at 36 atm, so as to have a constant syngas pressure of 1.0 MPa (10 atm) inside the reactor. After the reaction was started, 1:1 was fed throughout the course of the reaction, and a constant total pressure of 3.5 MPa (35 atm) was maintained in the reactor. The reaction was followed up in the same way as described in Example 1. 46% Ally) alcohol conversion was observed along with a 78.3% chemoselectivity to the aldehyde products, and n/iso ratio 11.72 was obtained. Overall TOF was calculated as 785 $h^{-1}$ at this conversion in 0.5 h.

EXAMPLE 6

2.401 g ($4.135 \times 10^{-2}$ moles) of allyl alcohol, and 0.045 g ($4.854 \times 10^{-5}$ moles) of $HRh(CO)(PPh_3)_3$ were taken in the 100 mL Hastelloy C Parr reactor and sealed. The contents were then flushed three times each with nitrogen, propane and syngas at ambient temperature. After the stabilization on addition of 2.6 MPa (26 atm) propane at 70° C. as described in Example 1, syngas ($H_2:CO=4:1$) was introduced and the reactor pressure was maintained at 36 atm, so as to have a constant syngas pressure of 1.0 MPa (10 atm) inside the reactor. After the reaction was started, 1:1 was fed throughout the course of the reaction, and a constant total pressure of 3.5 MPa (35 atm) was maintained in the reactor. The reaction was followed up in the same way as described in Example 1. Only 14.5% Allyl alcohol conversion was observed along with a 16.78% chemoselectivity to the aldehyde products, and n/iso ratio 5.6 was obtained. Overall TOF was calculated as 245 $h^{-1}$ at this conversion in 0.5 h.

What is claimed is:

1. A process for hydroformylating an olefinic feedstock, comprising forming a homogeneous reaction mixture including the olefinic feedstock, a hydroformylation catalyst and a single inert solvent, reacting the olefinic feedstock with carbon monoxide and with hydrogen in the presence of the catalyst under elevated temperature and pressure conditions sufficient to carry out a hydroformylation of the olefinic feedstock, then recovering substantially all of the solvent overhead as a vapor by reducing the pressure and degassing the product mixture.

2. A process according to claim 1, wherein the olefinic feedstock is derived from renewable sources.

3. A process according to claim 1 or 2, wherein the olefinic feedstock comprises allyl alcohol.

4. A process according to claim 1, wherein the single inert solvent is in a near critical state at the elevated temperature and pressure conditions in the reactor.

5. A process according to claim 4, wherein the single inert solvent is a liquefiable petroleum gas or a mixture of such gases.

6. A process according to claim 5, wherein the single inert solvent includes propane or butane.

7. A process according to claim 6, wherein the single inert solvent is propane.

8. A process according to claim 3, wherein the single inert solvent propane and wherein the elevated temperature and pressure conditions are such that the propane is in a near critical state.

9. A process according to claim 5, further comprising recompressing the petroleum gas or petroleum gas mixture and recycling the petroleum gas material or petroleum gas material mixture to the reaction vessel at substantially an original supply pressure and condition for reuse.

10. A process according to claim 1, further comprising recompressing and recycling the solvent in liquid form to the reaction vessel for reuse.

11. A process according to claim 1, wherein the hydroformylation catalyst comprises rhodium and is retained in the reaction vessel through the use of a nanofiltration membrane, following degassing of the single inert solvent and removal of hydroformylation products from the reactor through the membrane.

12. A process according to claim 11, wherein the catalyst comprises rhodium joined to a bulky, soluble phosphine or phosphate ligand which does not substantially pass through the nanofiltration membrane.

13. A process according to claim 1, wherein the desired hydroformylation product or products are substantially completely separated from the catalyst and solvent in successive steps.

14. A process according to claim 11, wherein the catalyst comprises a soluble polymeric support.

15. A process according to claim 2, wherein the carbon monoxide and hydrogen result from the gasification of biomass or methane reforming.

16. A process for hydroformylating allyl alcohol to products including 4-hydroxybutyraldehyde and 3-hydroxy-2-methylpropionaldehyde, comprising forming a homogeneous reaction mixture including allyl alcohol, a rhodium-based hydroformylation catalyst and a near-critical liquefiable petroleum gas or mixture of such gases, reacting the allyl alcohol with carbon monoxide and with hydrogen in the presence of the rhodium-based hydroformylation catalyst under elevated temperature and pressure conditions sufficient to carry out a hydroformylation of the allyl alcohol, then recovering substantially all of the petroleum gases overhead in a gaseous form by reducing the pressure and degassing the product mixture.

17. A process according to claim 16, carried out as a continuous process and wherein the relative production of 4-hydroxybutyraldehyde and 3-hydroxy-2-methylpropionaldehyde is adjusted online under otherwise steady state conditions, by limiting the allyl alcohol content in the reaction mixture.

18. A process according to claim 17, wherein the linear aldehyde product 4-hydroxybutyraldehyde is produced in a ratio of at least 10:1 to the branched aldehyde product 3-hydroxy-2-methylpropionaldehyde.

19. A process according to claim 16, conducted in the substantial absence of any solvent other than the liquefiable petroleum gas or mixture of such gases.

* * * * *